(12) United States Patent
Turner (10) Patent No.: US 10,125,270 B2
(45) Date of Patent: Nov. 13, 2018

(54) ANTI-MICROBIAL DRINKING OR EATING VESSEL

(75) Inventor: Alexander E. Turner, Great Massingham (GB)

(73) Assignee: AT Promotions LTD, Fakenham (GB)

( * ) Notice: Subject to any disclaimer, the term of this patent is extended or adjusted under 35 U.S.C. 154(b) by 853 days.

(21) Appl. No.: 14/396,923

(22) PCT Filed: Apr. 24, 2012

(86) PCT No.: PCT/GB2012/050900
§ 371 (c)(1),
(2), (4) Date: May 14, 2015

(87) PCT Pub. No.: WO2013/160630
PCT Pub. Date: Oct. 31, 2013

(65) Prior Publication Data
US 2015/0291806 A1    Oct. 15, 2015

(51) Int. Cl.
*A01N 25/34* (2006.01)
*C09D 5/14* (2006.01)
(Continued)

(52) U.S. Cl.
CPC ............ *C09D 5/14* (2013.01); *A01N 59/16* (2013.01); *A47G 19/02* (2013.01); *A47G 19/12* (2013.01);
(Continued)

(58) Field of Classification Search
CPC . C03C 17/326; C04B 41/009; C04B 41/4853; C04B 41/83
(Continued)

(56) References Cited

U.S. PATENT DOCUMENTS

| 4,966,815 A | 10/1990 | Hare |
| 4,993,987 A | 2/1991 | Hull et al. |

(Continued)

FOREIGN PATENT DOCUMENTS

| CN | 101305884 | 4/2008 |
| CN | 201542291 | 8/2010 |

(Continued)

OTHER PUBLICATIONS

GB Intellectual Property Office Search Report dated Oct. 20, 2014 for GB Application No. GB1407546.9, 5 pages.
(Continued)

*Primary Examiner* — Ellen S Wood
(74) *Attorney, Agent, or Firm* — Evan Law Group LLC (57) ABSTRACT

There is provided a drinking or eating vessel comprising an inner surface that defines a volume for receiving liquid or solid food and an outer surface that supports an anti-microbial coating and a decorative layer, wherein the anti-microbial coating comprises a polymer formed at a curing temperature of less than 600° C. and contains anti-microbial particles distributed within said coating, wherein the anti-microbial coating and/or the decorative layer define an outermost surface that is exposed to contact by a user of the vessel, and wherein the anti-microbial particles provide anti-microbial protection across the entire surface of said outermost surface. Also provided are corresponding process for producing the drinking or eating vessel.

16 Claims, 2 Drawing Sheets

(51) Int. Cl.
 A47G 19/12 (2006.01)
 A47G 19/22 (2006.01)
 C03C 17/34 (2006.01)
 C09D 5/16 (2006.01)
 C03C 17/00 (2006.01)
 A01N 59/16 (2006.01)
 A47G 19/02 (2006.01)

(52) U.S. Cl.
 CPC ......... *A47G 19/22* (2013.01); *A47G 19/2205* (2013.01); *C03C 17/003* (2013.01); *C03C 17/005* (2013.01); *C03C 17/3405* (2013.01); *C09D 5/1693* (2013.01); *A47G 2400/022* (2013.01)

(58) Field of Classification Search
 USPC ...................................... 428/34.1, 35.7, 174
 See application file for complete search history.

(56) References Cited

U.S. PATENT DOCUMENTS

| | | | |
|---|---|---|---|
| 5,246,518 | A | 9/1993 | Hale |
| 5,286,706 | A | 2/1994 | Mochizuki et al. |
| 5,643,387 | A | 7/1997 | Berghauser et al. |
| 6,217,694 | B1 | 4/2001 | Taniguchi |
| 9,856,055 | B2 | 1/2018 | Turner |
| 2005/0191569 | A1 | 9/2005 | Aylward et al. |
| 2007/0141125 | A1 | 6/2007 | Bourdelais et al. |
| 2011/0250405 | A1* | 10/2011 | Sawatsky ............. C03C 17/326 428/174 |
| 2015/0291806 | A1 | 10/2015 | Turner |

FOREIGN PATENT DOCUMENTS

| | | |
|---|---|---|
| CN | 201612433 | 10/2010 |
| CN | 202009965 | 10/2011 |
| DE | 40 11 215 | 10/1990 |
| EP | 0 227 092 | 7/1987 |
| EP | 0 350 534 | 1/1990 |
| EP | 0 420 986 | 4/1991 |
| EP | 0 474 355 | 3/1992 |
| EP | 0 514 631 | 11/1992 |
| EP | 0 543 441 | 5/1993 |
| EP | 0 587 148 | 3/1994 |
| EP | 0 672 542 | 9/1995 |
| EP | 0 721 848 | 7/1996 |
| EP | 1 024 180 | 6/2000 |
| EP | 1344760 | 9/2003 |
| EP | 15 723 281.0 | 3/2017 |
| GB | 1115663.5 | 1/2012 |
| GB | 2484774 A | 4/2012 |
| GB | 1115663.5 | 5/2014 |
| GB | 1115663.5 | 12/2014 |
| JP | 5-278745 | 10/1993 |
| JP | 8-333139 | 12/1996 |
| JP | 2004123462 | 4/2004 |
| KR | 20010078990 | 8/2001 |
| KR | 20080079832 | 9/2008 |
| WO | WO0053413 | * 3/2000 |
| WO | 2007/027710 | 3/2007 |
| WO | PCT/GB2012/00900 | 1/2013 |
| WO | 2013/160630 | 10/2013 |
| WO | PCT/GB2012/050900 | 4/2014 |
| WO | PCT/GB2012/050900 | 8/2014 |
| WO | 2015/166244 | 11/2015 |
| WO | PCT/GB2015/054134 | 3/2016 |
| WO | 2016/102963 | 6/2016 |
| WO | PCT/GB2015/054134 | 12/2016 |
| WO | PCT/GB2015/054134 | 4/2017 |

OTHER PUBLICATIONS

Database WPI Accession No. 1997-095320, Jan. 3, 2013.
International Search Reported dated Jan. 24, 2013 for PCT Application No. PCT/GB2012/050900, 3 pages.
GB Intellectual Property Office Search Report dated Jan. 10, 2012 for GB Application No. GB1115663.5, 2 pages.
U.S. Appl. No. 15/307,794, filed Apr. 4, 2017.
U.S. Appl. No. 15/307,794, filed Oct. 28, 2016, PCT/GB2015/051252, filed Apr. 29, 2015.
U.S. Appl. No. 15/539,062, filed Jun. 22, 2017, PCT/GB2015/054134, filed Dec. 22, 2015.
International Search Report and Written Opinion dated Mar. 3, 2016 for PCT Application No. PCT/GB2015/054134, 10 pages.
European Community Design Registration No. 02305375-0001, (Sep. 9, 2013).
European Community Design Registration No. 02305375-0002, (Sep. 9, 2013).
European Community Design Registration No. 02305375-0003, (Sep. 9, 2013).

* cited by examiner

ANTI-MICROBIAL DRINKING OR EATING VESSEL

The present invention relates to drinking or eating vessels having anti-microbial coatings, and to processes for producing such vessels. The present invention also relates to decorated drinking or eating vessels having anti-microbial coatings, and to processes for producing such decorated vessels.

A class of widely used products is drinking/eating vessels. By their nature, these vessels come into regular contact with the human body, including hands, faces and mouths. This permits the transfer of microbes from a human body to a drinking vessel, and from a drinking vessel to a human body. Furthermore, drinking and eating vessels may provide a surface on which microbes can grow. Thus, vessels of this type can facilitate the spread of microbes, including pathogenic microbes. This is undesirable and can be detrimental to people's health.

There is therefore a need for drinking or eating vessels which do not suffer from the above-described problems, and which can be used to prevent the unwanted spread of microbes.

Drinking and eating vessels are often decorated, for example with a decorative pattern or with an image such as a photographic image. There is therefore also a need for decorated drinking or eating vessels that do not suffer from the above-described problems, and which can be used to prevent the unwanted spread of microbes. In particular, it would be advantageous to provide a decorated drinking or eating vessel wherein the presence of a decoration does not compromise the prevention of the unwanted spread of microbes.

The present invention addresses one or more of the above-described problems by providing anti-microbial drinking or eating vessels and processes for producing said vessels, according to the present claims.

It is known in the art to provide drinking vessels that are coated, for example by a process of glazing. However, such glazing processes involve heating of the vessel and coating to a temperature of 650-1300° C.

In one aspect, the invention provides a drinking or eating vessel comprising an inner surface that defines a volume for receiving liquid or solid food and an outer surface that supports an anti-microbial coating and a decorative layer, (i) wherein the anti-microbial coating comprises a polymer formed at a curing temperature of less than 600° C. and contains anti-microbial particles distributed within said polymer,
(ii) wherein the anti-microbial coating and/or the decorative layer define an outermost surface that is exposed to contact by a user of the vessel,
(iii) and wherein said outermost surface provides anti-microbial protection across the entire surface thereof.

The term "drinking or eating vessel" includes vessels such as cups, mugs, bowls, and plates. The term "drinking or eating vessel" also includes storage vessels (for example, bottles and jars) of the type from which food products may be directly consumed.

The drinking or eating vessel may be made of any suitable material known in the art and may be of any suitable shape and design known in the art. In one embodiment, the vessel is a ceramic vessel. By way of example, the vessel may be made from bone china, porcelain, ceramics or stoneware. In one embodiment, the vessel is a glass vessel.

The vessel has an inner surface and an outer surface. The inner surface is found on the inside (during normal use) of the vessel, namely the portion in which liquid or solid food is received or held, or on which said food is supported. The outer surface is found on the external side (during normal use) of the vessel before any coating process of the invention has been applied. The outer surface includes the external surface provided by the body of a vessel and may include the external surface of any appendage (e.g. a handle) thereto. The outermost surface of the vessel represents a surface (following coating according to the present invention) that is exposed to contact by a user of the vessel (for example when the vessel is touched by the user during normal use associated with drinking or eating from the vessel).

The vessels of the invention have an anti-microbial coating. A coating is a layer of material that is applied onto a surface of the vessel. The anti-microbial coating may be applied to an outer surface of the vessel, or to an inner surface of the vessel, or to both an outer and an inner surface of the vessel.

The anti-microbial coating may be applied in any suitable and appropriate manner, for example by spray coating or by dip coating.

The anti-microbial coating may be a clear, colourless, transparent or translucent coating. Alternatively, the coating may be a coloured coating, for example to produce a coloured vessel in a corporate colour of a company.

The anti-microbial coating of the vessel is cured onto the outer surface (and/or inner surface) of the drinking vessel at a curing temperature of less than 600° C., for example less than 400° C. or less than 300° C. This class of polymer is well known to a skilled person.

In one embodiment, the coating is a coating that is produced by curing at a temperature of 180-220° C.

"Cured" and "curing" refers to the chemical process of curing, via which process a composition (typically containing monomers or small polymers) hardens (for example, due to the formation of cross-linking) when exposed to heat, air, ultraviolet radiation, infrared radiation or chemical additives. Thus, the coating may be produced by curing a coating mixture to form a hardened coating.

Thus, in one embodiment, the anti-microbial coating is produced by applying a coating mixture to a vessel followed by curing of the coating mixture at a temperature conducive to coating formation. A "coating mixture" comprises (or consists of) the ingredients that cure to form a coating on a vessel.

In one embodiment, the anti-microbial coating comprises (or consists of) a polymer formed at a curing temperature of less than 250° C.

The coating of the present invention comprises (or consists of) a non-glass layer (or non-glass coating).

For example, the coating may comprise (or consist of) one or more of: a polyurethane (lacquer or paint), an epoxy (resin), a polyester, an acrylic, or mixtures thereof. An epoxy may be a thermosetting copolymer that is formed by the reaction between an epoxide and a polyamine. The coatings may be provided as, for example, a water-based coating mixture or a solvent-based coating mixture.

In one embodiment, the coating comprises a cured polyurethane and/or a cured epoxy (resin). For example, the coating may comprise (or consist of) polyurethane. In one embodiment, the coating comprises (or consists of) an epoxy coating.

For example, the coating may comprise (or consist of) a polymeric blocked aliphatic diisocyanate epoxy coating, or an aliphatic (acrylic) polyurethane coating.

A typical epoxy (resin) composition may comprise (or consist of):

polyisocyanate (e.g. an aliphatic diisocyanate based polyisocyanate), for example 5-30 wt. %;
propylene glycol or ether acetate (e.g. a propylene glycol monomethyl ether acetate), for example 10-40 wt. %);
xylene (CAS No. 1330-20-7), for example 1-15 wt. %;
an organic solvent (e.g. solvent naptha), for example 1-10 wt. %;
an epoxy resin (for example, 5-20 wt. %).
Where wt. % values are indicated, said composition components add up to 100%.

An example of an epoxy (resin) composition comprises (or consists of):
methyl ethyl ketoxime-blocked aliphatic diisocyanate based polyisocyanate ≤30 wt %;
propylene glycol monomethyl ether acetate (CAS No. 108-65-6) ≤40 wt %;
xylene (CAS No. 1330-20-7)≤15 wt %;
aromatic 100 (solvent naptha) (CAS No. 64742-95-6) ≤10 wt %;
epoxy resin ≤20 wt %.
Where wt. % values are indicated, said composition components add up to 100%.

By way of specific example, reference is made to DuraGlaze, which is a polymeric blocked aliphatic diisocyanate epoxy resin.

Thus, the coating may comprise (of consist of) DuraGlaze.

A further example of an epoxy coating is Slotogard, which may be obtained from Schloetter Co Ltd, Abbey Works, New Road, Pershore, Worcs, UK.

A yet further example of an epoxy coating comprises (or consists of):
an ethanol component (e.g. 2-(2-butoxyethoxyl)ethanol), e.g. 5-5 wt. %;
an organic solvent component (e.g. xylene), e.g. 15-25 wt. %;
a butanol component (e.g. N-butanol), e.g. 1-5 wt. %;
epoxy resin (e.g. number average molecular weight ≤700), e.g. 25-50 wt. %.
Where wt. % values are indicated, said composition components add up to 100%.

An example of a suitable epoxy coating is Ceraglaze 51475, which may be obtained from Neogene LLP, Watford, Hertfordshire, United Kingdom.

Further examples of a polyurethane coating are Uraflex and Polysil SCW 700 Series, which may both be obtained from Schloetter Co. Ltd, Abbey Works, New Road, Pershore, Worcs, UK.

The coating may comprise an organic coating, such as a Transparent Stoving Finish (TSF). By way of example, a TSF may be a blend of polyurethane and epoxy resin.

A typical TSF may comprise (or consist of):
2-methoxy-1-methylethyl (CAS No. 108-65-6) 5-15%;
N-butyl acetate (CAS No. 123-86-4) 5-15%;
xylene (CAS No. 1330-20-7) 25-50%;
ethylbenzene (CAS No. 100-41-4) 5-15%;
epoxy resin (number average molecular weight ≤700) (CAS No. 25068-38-6) 1-5%.
Where wt. % values are indicated, said composition components add up to 100%.

Commercially available examples of TSFs are available from Neogene LLP, Watford, Hertfordshire, United Kingdom, such as TSF product code S1805.

The coating may comprise (or consist of) a polyester coating. An example of a polyester coating is Polysil SCW 800 Series, which may be obtained from Schloetter Co Ltd, Abbey Works, New Road, Pershore, Worcs, UK.

Other coating materials may be employed and are well known to a skilled person.

The anti-microbial coating is not a glass layer. For example, the anti-microbial coating of the present invention is not one that is obtained by glazing, which refers to heating a coating mixture at a temperature greater than 650° C. (for example, 1210° C.).

The anti-microbial coating may be a coating which is resistant to damage when the coated vessel is washed (for example, by hand, or in a dishwasher). Examples of such coatings include polyurethane lacquers/paints, epoxy resins and polymeric blocked aliphatic diisocyanate epoxy resins (e.g. DuraGlaze as described above).

The coated vessels of the invention comprise a decorative layer. A decorative layer comprises a decoration which covers all or part of a surface (typically at least part of the outer and/or inner surface) of the vessel, and may provide an aesthetic effect for the user.

The decorative layer may be a pattern or an image such as a photographic image. The decorative layer may be coloured. Thus, by way of example, the decorative layer may comprise patterns, texts, logos, advertisements, or other designs (e.g. corporate branding or trademarks), or combinations thereof. The decorative layer may comprise an image or images, such as pictures or photographic images.

The decorative layer may cover part of a surface of the drinking vessel. Alternatively, the decorative layer may cover all of a surface of the drinking vessel. A decorative layer may be applied to an outer surface, or to an inner surface (or to both), of a drinking vessel.

Examples of suitable techniques for producing decorative layers include:

Dye sublimation—a sublimation paper (comprising a desired image such as a photograph) is prepared using, for example, organic inks (as described below in more detail). The sublimation paper is cut to a desired shape and tightly wrapped around a coated vessel, before being subjected to heat (in order to set or cure the ink). This results in the inks becoming absorbed into the coating, to form a diffuse layer within said coating. By way of example, the inks may become gaseous and permanently dye the coating.

Colour coating—a coating mixture (for example, Transparent Stoving Finish) is mixed with coloured inks (for example, from Neogene, as described below in more detail) before being applied to a vessel and subjected to heat curing to form a coloured coating.

Screen printing—screen printing inks (for example, as described below) are screen printed or pad printed onto an uncoated vessel and heat- or air-cured. A coating is then applied on top of the decorative layer (as described above).

WoW mugs/vessels—an uncoated vessel is sprayed with a coloured thermochromic ink and heat cured to form a decorative layer that in use reacts with heat to change colour. The decorative layer may be a matt decorative layer. A coating (as described above) is then applied on top of the decorative layer.

Decal mugs/vessels—decal inks (for example, as described below) are printed onto Waterslide Decal Paper. When dry, the decal paper may be cut to the desired shape and transferred, using warm water, onto an uncoated vessel to form the decorative layer. A coating (as described above) is then applied on top of the decorative layer.

Any ink suitable for use on ceramic or glass may be used with the present invention.

An example of an ink suitable for use in a dye sublimation process is an organic (aqueous) ink. By way of example, the organic ink is an ink that is applied (e.g. sets or cures) at a temperature of up to 250° C., for example at a temperature of up to 222° C., or in the temperature range of 180-220° C.

Examples of such inks are available from Sawgrass Europe, Jubilee House, Hillsborough, Sheffield, S6 1LZ, United Kingdom. Examples may include Rotech Cyan, Magenta, Yellow, Black, Black Plus, Light Cyan, Light Magenta, and Light Black.

A further example of an ink suitable for use in dye sublimation is an ink-jet ink for transfer printing that is applied (e.g. sets or cures) at a temperature of up to 250° C., for example at a temperature of up to 220°, or in the temperature range 180-220° C. Examples of such inks are available from Sensient Imaging Technologies SA, Specialty Inks and Colors, ZI Riond-Bosson 8, 1110 Morges 2, Switzerland. An example of such an ink has the name S4 Subli Blue 770 (article No. 648770W).

An example of an ink suitable for use in a screen printing process is a screen and pad printing ink that is applied (e.g. sets or cures) at a temperature of up to 120° C., for example at 100° C. or less (e.g. at air temperature such as 40° C. or 30° C. or less). Such an ink may be based on epoxy resins and on solvents. An example of an ink suitable for use in a screen printing process may comprise one or more of: 4-hydroxy-4-methylpentan-2-one (e.g. 5-15 wt. %), solvent naphtha (heavy) (e.g. 5-10 wt. %); butyl glycolate (e.g. 5-10 wt. %); cyclohexanone (e.g. 5-10 wt. %). An ink suitable for use in a screen printing process may further comprise one or more of: 2-methoxy-1-methylethyl acetate (e.g. 5-10 wt. %); (2-methoxymethylethoxy)propanol (e.g. 1-10 wt. %); solvent naphtha (light) (e.g. 1-5 wt. %); naphtha (hydrotreated heavy) (e.g. 1-5 wt. %); dehydrogenated gum rosin (e.g. 1-5 wt. %). Examples of such inks are available from Pad Print Limited, 14 Enterprise Court, Park Farm North, Wellingborough, NN8 6UW. An example of such an ink has the name Glass Ink GL (product No. 3321).

An example of an ink suitable for use in a colour coat process are paints or inks that are applied (e.g. set or cure) at a temperature of up to 200° C., for example at a temperature of up to 180° C., such as in the temperature range of 160-180° C. Examples of such inks are from Neogene.

An example of an ink suitable for use in a decal mug/vessel process is Covercoat yellow, available from Dove Screen Services Limited, Trinity Road, Uttoxeter, Staffordshire, ST14 8SP (product No. DS8001).

The coated vessels of the invention comprise an anti-microbial coating. The anti-microbial properties are derived from the presence in the coating of an anti-microbial particle that comprises (or consists of) at least one anti-microbial agent.

The particles have sufficiently small dimensions to ensure substantially homogenous distribution throughout the anti-microbial coating. The particle may include a carrier, for example an inert particle meaning that it does not interfere with or otherwise adversely affect the integrity (e.g. strength and/or appearance) of the anti-microbial coating and/or the outermost surface. Simply for illustrative purposes, one example of a carrier is a titanium dioxide particle. Alternative carriers are well known to a skilled person. The anti-microbial agent may be coated onto or impregnated into an anti-microbial particle.

When incorporated within an anti-microbial coating component of the present invention, the anti-microbial particle retains an anti-microbial property after the curing process—in other words, the anti-microbial property of the particle is not destroyed during the curing process. Similarly, when incorporated within a decorative layer component of the present invention, the anti-microbial particle retains an anti-microbial property after the application process employed (which may, for example, include a heating or pressure application step)—in other words, the anti-microbial property of the particle is not destroyed during application of the decorative layer to the vessel.

An anti-microbial agent is a substance that is able to kill or inhibit the growth of microorganisms (also known as microbes), for example bacteria, viruses, fungi and protozoa. Thus, the application of anti-microbial particles to a vessel in accordance with the present invention enables the killing, colonisation inhibition, or growth inhibition of microorganisms (such as pathogenic or disease-causing microorganisms) that may contact said vessel. This advantageously reduces or prevents the spread of microorganisms and therefore reduces or prevents the incidence and spread of diseases caused by microorganisms.

In one embodiment, the anti-microbial particle comprises (or consists of) an anti-bacterial agent.

More than one different type of anti-microbial agent, for example two, three, four or five anti-microbial agents, may be employed in the context of the present invention and thus applied to the same vessel. In this regard, use of multiple different anti-microbial agents may be employed to increase the range of microorganisms to be targeted.

The same or different anti-microbial agent(s) may be employed in the anti-microbial coating component, and in the decorative layer component of the present invention.

Any suitable and appropriate anti-microbial agent may be employed for preventing or hindering the spread of any relevant infection, for example, bacterial infections, microbial infections, and viral infections. In use, the anti-microbial agent may exert its effect by destabilising microbial cell membrane and/or cell wall integrity, by suppressing nucleic acid or protein synthesis, by suppressing cell division, and/or by starving the microbes of nutrients that they would require to thrive and proliferate.

The anti-microbial agent or agents used in the present invention may be effective against one or more of *Clostridium difficile*, methicillin-resistant *Staphylococcus aureus* (MRSA), *Listeria monocytogenes, Salmonella* species, enteritis-causing microorganisms, *Escherichia coli, Bacillus cereus, Aspergillus niger, Pseudomonas aeruginosa, Klebsiella pneumonia, Saccharomyces cerevisiae,* and *Penicillium purpurogenum*. Preferred microbial targets of the present invention are gastro-intestinal disease-causing bacteria.

The anti-microbial particles are typically incorporated into the anti-microbial coating by a pre-mixing step prior to application of the coating mixture to the vessel. The anti-microbial coating may then be formed by curing said mixture—the curing temperature is selected to ensure adequate coating formation has been achieved, whilst ensuring that the anti-microbial agent retains adequate anti-microbial activity. Said pre-mixing step ensures that the anti-microbial particles are distributed throughout the coating.

The coating and/or the decorative layer of the present invention provide an outermost surface that is typically exposed to contact by a user (during normal use) of the vessel.

In one embodiment, said outermost surface has anti-microbial particles distributed across the entire surface thereof. Thus, the entire outermost surface of the vessel may have anti-microbial properties due to the presence of the anti-microbial agent across the entire outermost surface.

In one embodiment, the decorative layer provides at least part of an outermost surface that is exposed to contact by a user (during normal use) of the vessel, said outermost surface having anti-microbial particles distributed across the entire surface thereof.

In one embodiment, the decorative layer forms a diffuse layer within at least part of the anti-microbial coating. Thus, in one embodiment, a decorative layer is formed (for example, by dye sublimation) as an integral part of the coating. Thus, advantageously, the presence of the decorative layer does not compromise the anti-microbial agent from exerting its anti-microbial effect at the outermost surface of the drinking vessel. Accordingly, a decorative layer may be incorporated into the vessel, which maintains optimal anti-microbial capacity at the outermost surface local to (e.g. in the immediate vicinity of) the decorative layer. This therefore negates the need for application of a separate/subsequent anti-microbial coating at the outermost surface local to (e.g. in the immediate vicinity of) the decorative layer.

In one embodiment, the anti-microbial agent comprises silver. In one embodiment, the anti-microbial agent comprises (or consists of) silver chloride. Silver chloride is known to have anti-microbial effects, which have been attributed to the anti-microbial properties of silver ions. Accordingly, other silver halides may be similarly employed.

Other anti-microbial agents are suitable for use in the present invention, for example anti-microbial agents containing metals other than silver. Non-limiting examples include anti-microbial agents comprising one or more of the following metals: mercury, copper, iron, lead, zinc, bismuth, gold, and aluminium. Chlorides and other halides of these metals may be similarly employed.

The anti-microbial agent may be incorporated as part of a slow release anti-microbial particle. Thus, in one embodiment, the anti-microbial agent is provided in a form in which the active constituent is released at a controlled rate, thus increasing the lifetime of the anti-microbial agent and making it more effective.

By way of example, anti-microbial agent may be coated onto titanium oxide particles, which act as a carrier and provides slow release properties. Other suitable metal oxide carrier particles may be similarly employed, and include one or more of sodium antimony oxide, zinc iron manganese titanium oxide, iron titanium oxide, manganese antimony oxide, and manganese titanium oxide.

In one embodiment, the anti-microbial agent comprises (or consists of) titanium oxide particles coated with silver chloride. Said coated particles advantageously have slow release properties.

In one embodiment, the anti-microbial agent is stable (i.e. it retains anti-microbial efficacy) after having been heated to a temperature up to 600° C.

In one embodiment, the anti-microbial coating is a coating that is produced by curing at a temperature of 600° C. or less. Accordingly, the anti-microbial agent employed for use in said coating is stable at the elected temperature.

In one embodiment, the coating is a coating that is produced by curing at a temperature of 180-220° C. Accordingly, the anti-microbial agent employed for use in said coating is stable at the elected temperature.

By way of example, epoxy coatings such as Ceraglaze S1475 typically cure in 8-14 minutes at a temperature of 180-220° C.

In one aspect, the invention provides a process for producing a drinking or eating vessel having an integral anti-microbial coating, wherein the vessel comprises an inner surface that defines a volume for receiving liquid or solid food and an outer surface that supports an anti-microbial coating and optionally a decorative layer, said process comprising the steps of:

providing a coating mixture that comprises anti-microbial particles, wherein said coating mixture forms the anti-microbial coating upon curing at a temperature of less than 600° C., applying said coating mixture to the outer surface of the drinking or eating vessel, curing the coating mixture to form said anti-microbial coating wherein the anti-microbial coating defines an outermost surface that is exposed to contact by a user of the vessel, and wherein said outermost surface provides anti-microbial protection across the entire surface thereof.

In one embodiment, the coating mixture is cured at a temperature of less than 250° C., or at a temperature in the range of 150-300° C. (e.g. in the range of 180-220° C.).

The coating mixture may be cured for a period of time of between 1 and 30 minutes, for example, 5-25 minutes, 5-20 minutes, 10-20 minutes, or 10-15 minutes.

The anti-microbial agent for use in the process of the invention may be any anti-microbial agent as described above.

Anti-microbial agents are readily damaged by excess heat, such that they become degraded and exhibit reduced or no anti-microbial efficacy. Prior art methods of applying coatings to drinking vessels employ glazing processes, which involve heating steps at temperatures that are detrimental to efficacy of the anti-microbial agent (for example, heating at 650-1300° C.). In contrast the present invention employs curing (rather than glazing) temperatures, which preserve efficacy of the antimicrobial agent.

The present invention provides coated vessels having anti-microbial particles distributed substantially across the entire outermost surface. This ensures that all parts of the vessel which come into user contact (during normal use) have good anti-microbial properties.

In certain embodiments, the curing process requires heat. The heat required for the curing process may be provided by, for example, infrared radiation (such as in an infrared oven), or by convection (such as in a convection oven). Alternatively, curing may be effected by air in a process of air curing.

The coating mixture (and thus the resultant coating) may comprise the anti-microbial agent at a concentration of 0.1 to 5 wt. %, for example 0.1 to 1 wt. %, 0.1 to 0.5 wt. %, or 0.3 to 0.5 wt. %. By way of example, the coating mixture (and thus the resultant coating) may comprise the anti-microbial agent at a concentration of 0.1, 0.2, 0.3, 0.4, 0.5, 0.6, 0.7, 0.8, 0.9, 1.0, 2.0, 3.0, 4.0 or 5.0%.

In one embodiment, the anti-microbial coating mixture is applied to a vessel already having a decorative layer present on the outer surface, such that the coating forms the outermost surface of the vessel. Thus, the coating overlays said decorative layer. The coating may be transparent (or equivalent), in order for the decorative layer to remain visible. Advantageously, the resulting vessel demonstrates an uncompromised anti-microbial outermost layer.

In one embodiment, the process of the invention provides a vessel having an anti-microbial coating applied to the outer surface. Said process may further comprise the steps of: providing a decorative mixture, and applying (e.g. by dye sublimation) the decorative mixture to the drinking vessel, such that the decorative mixture forms a diffuse decorative layer within the anti-microbial coating. Thus, the anti-microbial coating incorporates the decorative layer, which is impregnated into at least part of the anti-microbial coating itself. Advantageously, the resulting vessel demonstrates an uncompromised anti-microbial outermost layer.

In one embodiment, the process of the invention provides a vessel having an anti-microbial coating applied to the outer surface. Said process may further comprise the steps of: providing a decoration mixture comprising anti-microbial particles, and applying said decoration mixture to the drinking vessel to form a decorative layer. Thus, in this embodiment, the decorative layer and/or the anti-microbial coating provide the outermost surface. Advantageously, the resulting vessel demonstrates an uncompromised anti-microbial outermost layer.

In one further aspect, the invention provides a drinking vessel obtainable by a process as hereinbefore described.

The temperature values/ranges described herein with reference to the drinking/eating vessel aspect apply equally to the coating step of the process aspect.

Reference herein to "liquid or solid food" embraces any item that a mammal (e.g. a human) might drink or eat. Said item may have any (including zero) calorific value.

Reference herein to "an inner surface that defines a volume for receiving liquid or solid food" embraces any structure that is capable of supporting a liquid or solid food item. Said structure may include plates and plate-like articles of manufacture (whether flat or curved in vertical cross-section), and bowls or bowl-like articles of manufacture (whether capable of retaining liquid or not).

Reference herein to "supports" simply indicates that an anti-microbial coating has been applied to the outer (and/or inner) surface of the vessel. Thus, the anti-microbial coating may directly contact the outer (and/or inner) surface and/or may be separated therefrom by one or more intervening layers/coatings.

Reference to "outermost surface" when used in the context of anti-microbial coating and/or decorative layer applied to the outer surface of the vessel means the resulting exposed surface(s) that would come into contact with a user of the vessel (during normal eating and/or drinking use from the vessel)—such external surfaces include any handle or equivalent (if present), the side(s) or equivalent of the vessel, and the drinking lip/edge or equivalent of the vessel (e.g. the structure formed where the inner and outer surfaces meet), and optionally include any base surface that might be used to support the vessel, for example when free-standing or when held by a user. Reference to "outermost surface" when used in the context of anti-microbial coating and/or decorative layer applied to the inner surface of the vessel means the resulting exposed surface(s) that, in use, would contact with liquid or solid food introduced into the vessel (during normal eating and/or drinking use from the vessel).

In one embodiment, the coating does not comprise (or consist of) any one or more of polyurethane acrylic ester, benzoin ethyl ester, dimethyl ethanolamine, silica tourmaline, or silica nano-silver.

Embodiments of the invention will now be described solely by way of example and with reference to the accompanying drawings.

Figure 1:
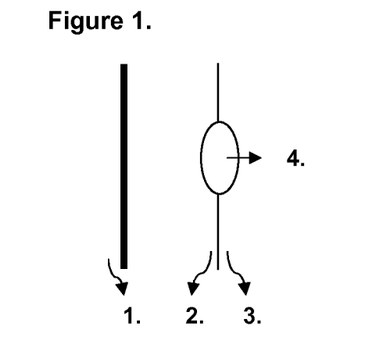
FIG. 1 illustrates part of a vessel having on its outer surface 1 a coating 3 comprising an anti-microbial agent 4.

Photo Mug:

Referring to FIG. 1, there is shown part of a vessel having on its outer surface 1 a coating 3 comprising an anti-microbial agent 4. The coating has been formed by providing a coating mixture (such as that which produces a DuraGlaze coating) and mixing with it an anti-microbial agent. Said coating mixture has then been applied to the vessel by spraying (or dipping), before heat curing at a temperature below a temperature which will lead to reduced efficacy of the anti-microbial agent. The coating 3 has, as an integral part, a decorative layer 2, which has been formed by a dye sublimation image which has permanently dyed the coating 3. Said dye sublimation image has been applied to the coated vessel and subjected to a further heating process, causing the inks to permanently dye the coating.

Figure 2:
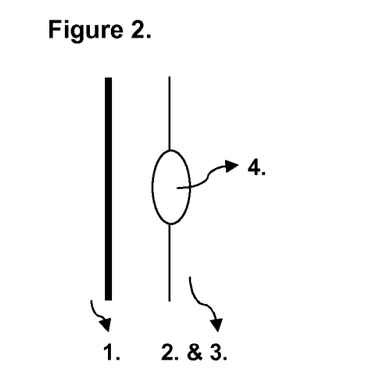
FIG. 2 illustrates part of a vessel having on its outer surface 1 a coating 2 comprising and anti-microbial agent 4.

ColourCoat Mug:

Referring to FIG. 2, there is shown part of a vessel having on its outer surface 1 a coating 2 comprising and anti-microbial agent 4. The coating may comprise Transparent Stoving Finish into which has been mixed Neogene inks to provide colour, and which has further been mixed with ant-microbial agent 4.

Figure 3:
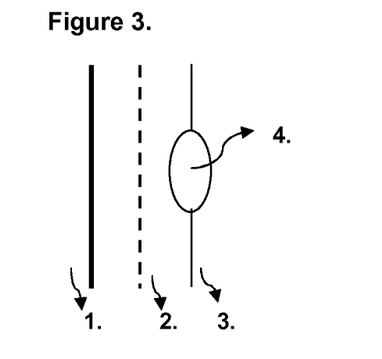
FIG. 3 illustrates part of a vessel having on its outer surface 1 a decorative layer 2, which is a screen/pad printed image on the mug surface 1, and a coating 3, which is Transparent Stoving Finish, in which coating 3 contains an anti-microbial agent 4.

Screen Print Mugs (Types 1 & 2):

Referring to FIG. 3, there is shown part of a vessel having on its outer surface 1 a decorative layer 2, which is a screen/pad printed image on the mug surface 1, and a coating 3, which is Transparent Stoving Finish, in which coating 3 is distributed an anti-microbial agent 4.

Figure 4:
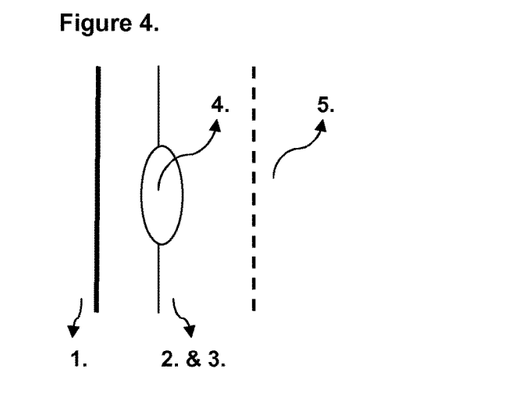
FIG. 4 illustrates part of a vessel having on its outer surface 1 a coating 2 (which in this example is Transparent Stoving Finish), in which coating 2 contains an anti-microbial agent 4.

Screen Print Mugs (Type 3):

Referring to FIG. 4, there is shown part of a vessel having on its outer surface 1 a coating 2 (which in this example is Transparent Stoving Finish), in which coating 2 is distributed an anti-microbial agent 4. Said coating 2 has also had mixed within a coloured inks, thus providing an integral decorative layer 3. On top of coating 2 is provided a further decorative layer 5, which comprises screen print inks which have been mixed with anti-microbial agent.

Figure 5:
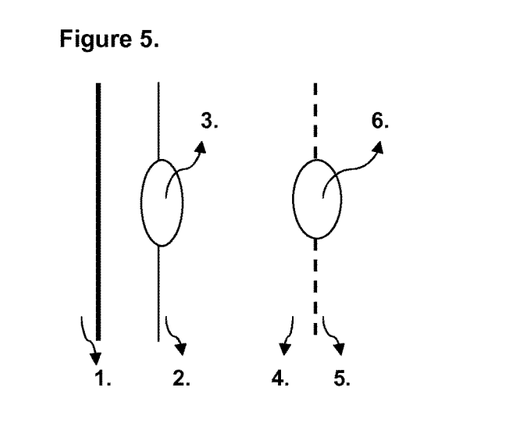
FIG. 5 illustrates part of a vessel having on its outer surface 1 a decorative layer, which comprises a water-based stoving finish 2 which has been mixed with a thermochromic ink 3, and a coating comprising an integral decorative layer is provided, which comprises a Transparent Stoving Finish 5 mixed with anti-microbial agent 6 and a dye sublimation decoration 4 dyed into the Transparent Stoving Finish.

WoW Mug:

Referring to FIG. 5, there is shown part of a vessel having on its outer surface 1 a decorative layer, which comprises a water-based stoving finish 2 which has been mixed with a thermochromic ink 3. A coating comprising an integral decorative layer is provided, which comprises a Transparent Stoving Finish 5 mixed with anti-microbial agent 6 and a dye sublimation decoration 4 dyed into the Transparent Stoving Finish.

Figure 6:
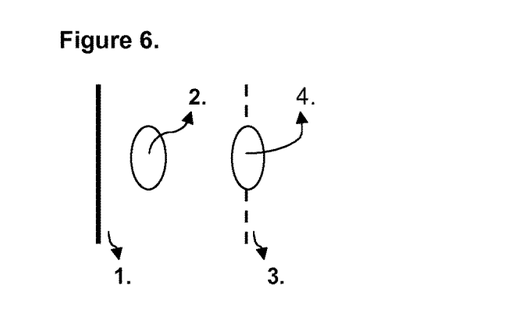
FIG. 6 illustrates part of a vessel having on its outer surface 1, a decorative layer 2 which comprises a decal transfer, and on top of said decorative layer 2 a coating 3 is provided, which comprises Transparent Stoving Finish, which contains an anti- microbial agent 4.

Decal Mugs:

Referring to FIG. 6, there is shown part of a vessel having on its outer surface 1 a decorative layer 2 which comprises a decal transfer. On top of said decorative layer 2 is provided a coating 3, which comprises Transparent Stoving Finish, into which is distributed anti-microbial agent 4.

It is to be appreciated that the embodiments of the invention described above with reference to the accompanying drawings have been given by way of example only and that modifications may be effected.

EXAMPLES

Photo Mugs—

DuraGlaze® is mixed with the anti-microbial agent at a rate of 0.3% to 0.5% by weight. This lacquer/paint is then sprayed onto a blank mug and cured in the range of 180° C. to 220° C.

Sublimation papers are then printed using inks from Sawgrass, Sensient or other suitable brands known to those skilled in the art. They are cut to shape and tightly wrapped round the cured DuraGlaze® mug and heated in a mug oven in the range of 180° C. to 220° C. During the heating process the inks become gaseous and permanently dye the DuraGlaze® coating (or any other coating described above). (see FIG. 1.).

Colour Coat Mugs—

The Transparent Stoving Finish is mixed with coloured inks from Neogene to produce whatever colour is desired (e.g. a corporate colour). Those coloured coatings then have the anti-microbial agent mixed in at a rate of 0.3% to 0.5% by weight. The coating is then sprayed onto blank mugs and cured in the range of 180° C. to 220° C. and cooled (see FIG. 2.).

Screen Print Mugs (Type 1)—

Using Screen Printing inks from Pad Print Ltd. These inks can be Screen Printed or Pad Printed onto a plain mug with no coating. They are cured at 110° C. (or Air Cured) and then sprayed with the Transparent Stoving Finish which contains the anti-microbial agent mixed at 0.3% to 0.5% by weight. They are cured at 180° C. to 190° C. and although this is a higher curing temperature than the inks it does not affect those inks (see FIG. 3.).

Screen Print Mugs (Type 2)—

Using Screen Printing inks manufacture by, e.g. Dove Services, or Johnson Matthey. These inks can be Screen Printed onto a plain mug with no coating. They are cured in the range of 800° C. to 850° C. and after cooling they are sprayed with the Transparent Stoving Finish which contains the anti-microbial agent mixed at 0.3% to 0.5% by weight. They are then cured in the range of 180° C. to 190° C. (see FIG. 3.).

Screen Print Mugs (Type 3)—

Using Screen Printing inks from Pad Print Limited to be Screen Printed onto a ColourCoat mug that already contains the anti-microbial agent (see ColourCoat Mugs). The inks are mixed with the anti-microbial agent at 0.3% to 0.5% by weight. They are then screen printed onto a ColourCoat mug and cured at 110° C. or air cured (see FIG. 4.).

WoW Mugs—

A blank mug is sprayed with a water based (or solvent based) stoving finish mixed with a coloured thermochromic ink (for example, manufactured by Matsui, Japan) and cured in the range of 180° C. to 220° C. This produces a coloured WoW mug that has a matt finish. A Transparent Stoving Finish is then sprayed onto the matt surface to give a gloss finish, this Transparent Stoving Finish contains the anti-microbial agent mixed at 0.3% to 0.5% by weight and cured at 180° C. to 220° C.

If a Dye Sublimation decoration is desired then the same steps as Photo Mugs are taken. (see FIG. 5.).

Decal Mugs—

Decal Inks from Dove Services are printed onto a specialist paper known as Waterslide Decal Paper. When dry they are cut to the design shape and transferred, by hand, onto a mug using warm water. The Transparent Stoving Finish is then mixed with the anti-microbial agent at a rate of 0.3% to 0.5% by weight and sprayed onto the mug (see FIG. 6.).

Anti-Microbial Efficacy

The anti-microbial properties of coated vessels of the present invention were tested in comparison to control samples lacking any anti-microbial particles. Results are presented as CFU cm$^{-2}$. The anti-microbial agent in each case is silver chloride, as described above.

| Sample | Species | Contact time | | Reduction (control) | |
| --- | --- | --- | --- | --- | --- |
| | | 0 hrs | 24 hrs | Log 10 | % |
| Polystyrene | E. coli | 1.1E+04 | 3.5E+05 | | |
| Treated blue mug | E. coli | 1.1E+04 | 1.1E+03 | | 99.68 |
| Ceramic | MRSA | 1.6E+04 | 2.5E+04 | | |
| Treated blue mug | MRSA | 1.6E+04 | 7.7E+02 | 2.7 | 99.82 |
| Treated white mug | MRSA | 1.6E+04 | <25.00 | ≥2.99 | ≥99.90 |
| Polystyrene | E. coli | 1.1E+04 | 3.5E+05 | | |
| Treated white mug | E. coli | 1.1E+04 | <25.00 | ≥4.15 | ≥99.99 |

In each case, a significant and pronounced anti-microbial effect is demonstrated, with a reduction in bacterial contamination of the drinking vessel of greater than 99% as compared to a control.

The invention claimed is:

1. A drinking or eating vessel comprising an inner surface that defines a volume for receiving liquid or solid food and an outer surface that supports an anti-microbial coating and a decorative layer,
   (i) wherein the anti-microbial coating comprises a polymer formed at a curing temperature of less than 600° C. and contains anti-microbial particles distributed within said coating,
   (ii) wherein the anti-microbial coating defines an outermost surface that is exposed to contact by a user of the vessel,
   (iii) wherein the anti-microbial particles provide anti-microbial protection across the entire surface of said outermost surface,
   (iv) wherein the decorative layer forms a diffuse layer within the anti-microbial coating,
   (v) wherein the drinking or eating vessel comprises a material selected from the group consisting of bone china, porcelain, ceramics, stoneware and glass, and
   (vi) wherein the anti-microbial particles are not present on the inner surface.

2. The drinking or eating vessel of claim 1, wherein the anti-microbial particles comprise metal oxide particles.

3. The drinking or eating vessel of claim 1, wherein the anti-microbial particles comprise a slow release agent that controls the release of an anti-microbial agent component from the anti-microbial particles.

4. The drinking or eating vessel of claim 1, wherein the anti-microbial particles comprise a silver compound.

5. The drinking or eating vessel of claim 1, wherein the anti-microbial particles comprise metal oxide particles coated with a silver compound.

6. The drinking or eating vessel of claim 1, wherein the anti-microbial coating comprises a polymer formed at a curing temperature of 180-220° C.

7. The drinking or eating vessel of claim 1, wherein said vessel comprises ceramic and/or glass.

8. The drinking or eating vessel of claim 1, wherein the antimicrobial coating comprises a polymer selected from the group consisting of a polyurethane, an epoxy, a polyester, an acrylic, and mixtures thereof.

9. The drinking or eating vessel of claim 1, wherein the decorative layer comprises a pattern or an image.

10. The eating or drinking vessel of claim 1, wherein the anti-microbial particles comprise a silver compound or metal oxide particles coated with a silver compound,
   wherein the anti-microbial coating comprises a polymer selected from the group consisting of a polyurethane, an epoxy, a polyester, an acrylic, and mixtures thereof,
   wherein the polymer is formed at a curing temperature of 180-220° C., and
   wherein the decorative layer comprises a pattern or an image.

11. A drinking or eating vessel, comprising:
   an inner surface that defines a volume for receiving liquid or solid food,
   an outer surface, and
   a decorative layer on the outer surface,
   wherein the drinking or eating vessel comprises a material selected from the group consisting of bone china, porcelain, ceramics, stoneware and glass,
   the decorative layer comprises
      (i) a polymer,
      (ii) anti-microbial particles, and
      (iii) a dye or ink, and
   the anti-microbial particles are not present on the inner surface.

12. The drinking or eating vessel of claim 11, wherein the anti-microbial particle comprises a silver compound.

13. The drinking or eating vessel of claim 11, wherein the dye or ink comprises an organic dye or an ink-jet ink.

14. A drinking or eating vessel, comprising:
   an inner surface that defines a volume for receiving liquid or solid food,
   an outer surface,
   a dye or ink, on the outer surface
   anti-microbial particles, on the outer surface, and
   a polymer, on the outer surface,
   wherein the drinking or eating vessel comprises a material selected from the group consisting of bone china, porcelain, ceramics, stoneware and glass, and the anti-microbial particles are not present on the inner surface.

15. The drinking or eating vessel of claim 14, wherein the anti-microbial agent comprises a silver compound.

16. The drinking or eating vessel of claim 14, wherein the dye or ink comprises an organic dye or an ink-jet ink.

* * * * *